United States Patent [19]

Chan et al.

[11] 4,138,422
[45] Feb. 6, 1979

[54] METHOD OF PRODUCING BIOLOGICALLY ACTIVE COMPOSITIONS

[75] Inventors: John K. Chan, St. Albans; Erich Tobler, Charleston, both of W. Va.; Herbert E. Johnson, Hong Kong

[73] Assignee: Union Carbide Corporation, New York, N.Y.

[21] Appl. No.: 491,346

[22] Filed: Jul. 24, 1974

[51] Int. Cl.$^2$ .................... C07C 69/00; A01N 9/20
[52] U.S. Cl. .................... 260/453 RW; 260/553 A; 560/16; 560/24; 560/148; 560/157; 424/300
[58] Field of Search .......... 260/471 C, 482 C, 553 A, 260/453 RW; 560/16, 24, 148, 157; 424/300

[56] References Cited

U.S. PATENT DOCUMENTS

| | | | |
|---|---|---|---|
| 3,398,106 | 8/1968 | Hostettler et al. | 260/482 C |
| 3,449,406 | 6/1969 | Goodman et al. | 260/482 C |
| 3,576,834 | 4/1971 | Buchanan | 260/482 C |
| 3,625,993 | 12/1971 | Horn | 260/482 C |

OTHER PUBLICATIONS

Chemical Abstracts, vol. 72 (1970), p. 16096h.
Chemical Abstracts, vol. 78 (1973), p. 14,957q.

*Primary Examiner*—V. D. Turner
*Attorney, Agent, or Firm*—Robert C. Brown

[57] ABSTRACT

Biologically active compositions are prepared by reacting an active hydrogen containing precursor with an isocyanate compound in the presence of solid particulate matter.

28 Claims, No Drawings

METHOD OF PRODUCING BIOLOGICALLY ACTIVE COMPOSITIONS

This invention is directed to a method of producing biologically active compositions by reacting an active hydrogen containing precursor compound and an isocyanate compound in the presence of granular substrate material to yield a solid particulate product in which the active agent is formed directly on the particulate substrate.

A large number of pesticidal compositions commonly used at this time are of the carbamate or urea type in which it is customary to form the carbamate or urea moiety in the last step of the chemical process by reacting a suitable isocyanate composition with an appropriate active hydrogen containing precursor. Thus, for example; Methamyl is prepared by reacting 1-Methylthioacetaldoxime with methyl isocyanate (MIC) to produce 1-Methylthioacetaldehyde O-(methylcarbamoyl) oxime and Aldicarb is prepared by reacting 2-methyl-2-(methylthio)propionaldehyde oxime and methyl isocyanate to form 2-methyl-2-(methylthio)-propionaldehyde O-(methylcarbamoyl) oxime.

Such biologically active compositions commonly have a very high degree of activity which makes it necessary for them to be diluted prior to use for both practical and economic reasons. Among the various compounds in use at the present time as insecticides, acaracides, nematocides, fungicides, bacteriocides and herbicides are many which are extremely hazardous to forms of life other than the intended application. Most of such biologically active substances are considerably safer to handle in dilute form.

Because of these factors it has become common practice to dilute the concentrated active agent by impregnating it into or on a solid substrate, such as finely divided clay, peat, mica, vermiculite, coal, ground corn cobs, walnut shells, redwood bark and the like. The use of a solid diluent is preferred for safety and practical reasons. Liquid formulations of highly active substances generally pose a greater safety and handling problem than do solid diluents due to the risk of spillage, drift in application and like problems.

In present day commercial practice, to produce such dilute granular products it is necessary to prepare the active ingredient in solution, in accordance with conventional chemical procedures, followed by impregnation of the solid substrate with a solution of the active ingredient, as a separate step, and thereafter removing the solvent to produce the desired granular product.

The process of the present invention eliminates impregnation as a separate step, which is highly desirable for economic reasons. Because many chemical substances which are capable of being produced by this process are toxic materials, this invention enjoys significant advantages over prior art methods in terms of safety considerations. In most cases the individual isocyanate and active hydrogen containing reactant are relatively non-toxic. By the use of this process the resulting toxic product is never present except in dilute form. The product is never present nor is there any need to handle it in pure or concentrated form. The product molecules form on and adhere to the substrate thus minimizing the possibility of contamination by vaporization or leaking. In addition the particle size can be controlled to prevent contamination by airborne particles.

It is usual in the conventional process of preparing granular formulations of biologically active compositions to incorporate a resinous or adhesive substance into the granular formulation as a dust binding agent. A feature of the present invention resides in the discovery that in most cases it is possible to reduce substantially or possibly eliminate such dust binding agents and still achieve the necessary control over particle size, particularly, the avoidance of very small particles capable of being air borne contaminates.

In the novel process of this invention two reactants, one being a composition having an active hydrogen and the other being a composition carrying an isocyanate substituent are reacted in the presence of a granular solid preferably in the absence of any solvent or other liquid diluent.

Any reactive hydrogen containing compound capable of reacting with an isocyanate compound can be used as one of the reactants in accordance with this invention. Examples of such reactive hydrogen containing compounds are:

1. Aliphatic alcohols such as: ethanol, isopropanol, 1-undecanol, methoxymethanol, methylthioethanol, hydroxymethylethylketone.

2. Aromatic aliphatic alcohols such as: benzyl alcohol and 3,4 dichlorobenzyl alcohol.

3. Phenolic compounds such as: phenol, naphthol, cresol, xylenol.

4. Thiol compounds such as: methylmercaptan, ethylmercaptan, thiophenol, thionaphthol.

5. Ammonia and secondary and primary amine compounds such as: methylamine, ethylamine, dimethylamine, diethylamine.

6. Oxime compounds such as: acetaldoxime, butylaldoxime, cyclododecanone oxime, 2-oximino-1,4-dithiane.

The active hydrogen carrying compound may be substituted with one or more various substituents such as alkyl, chlorine, fluorine, bromine, nitro, cyano, haloalkyl, alkoxy, alkylthio, alkanoyl and the like, the only limitation on substituents being that there should not be more than one substituent capable of reacting with isocyanate unless multiple reactions are desired, as for example in the case where it desired to produce a dicarbamate composition by reacting a diol composition with an isocyanate compound.

Any composition having a reactive isocyanate group and no other substituents capable of reacting with an active hydrogen group can be used as the isocyanate compound. Such compositions include, for example:

1. Aromatic isocyanate compositions such as: phenylisocyanate, chlorophenylisocyanate, toluenediisocyanate.

2. Aliphatic isocyanate compositions such as: methylisocyanate, ethylisocyanate, propylisocyanate, butylisocyanate.

3. Aliphatic aromatic compositions such as: benzylisocyanate and 4-methylbenzylisocyanate.

The isocyanate composition may also be substituted with one or more of a variety of substituents such as alkyl, chlorine, fluorine, bromine, nitro, cyano, haloalkyl, alkoxy, alkylthio, alkanoyl and the like, the only limitation on substituents being that they should be incapable of reacting with an active hydrogen. It will be understood however that where a dicarbamate is desired a diisocyanate can be used. In general the use of diisocyanate reactant with a compound having more than one active hydrogen is to be avoided as a polymeric product will result.

While specific classes of reactants have been described above it should be understood the process of the present invention can be employed using any combination of isocyanate and active hydrogen reactants which are capable of being reacted to produce useful products by conventional solution processes.

When both reactants are liquids at the desired reaction temperature no solvent is required. It is preferable in the practice of this invention to avoid the use of solvent as this eliminates the need for the additional step of solvent removal from the finished product. In those cases where one or both of the reactants is solid or gaseous at the desired reaction temperature, minimal amounts of a low boiling solvent such as acetone, chloroform or acetonitrile should be used to dissolve the solid or gaseous reactant to assure complete and intimate mixing of the reactants.

To simplify purification of the final granular product it is preferable to employ a slight excess of the more volatile reactant to insure complete conversion of the less volatile reactant.

Conventional catalysts, such as trimethylamine, trethylamine and dibutyltin acetate may be employed if desired. Volatile catalysts such as trimethylamine are preferred. Although the use of a catalyst is preferred, the reaction will proceed without catalysis but at a somewhat slower rate. Some of the solid granular materials used in accordance with this invention may be mildly catalytic due to the provision of reaction sites.

The solid granular substrate can be any of the materials commonly used for this purpose in conventional impregnation processes. These include clays, peat, mica, vermiculite, coal, ground corncobs, tobacco skins, coconut shells, walnut shells, wood flour, redwood bark and like materials. Particle size is not critical but will generally range from about 10 to about 60 mesh. Very fine dust particles can be used as the substrate, if desired, as the product can be made to agglomerate by the use of high concentrations of binder, up to about 30% which produces large granules. Should a plug of product result or should the product granule size be too large the product can be ground and screened to obtain the desired particle size.

The use of a resinous or adhesive binding agent is preferred in the conduct of this process to prevent dust formation of the toxicant. Up to about 30% by weight based on active ingredient, of binding agent can be used if desired. Any conventional binding material which is soluble in at least one of the reactants can be used. Vinyl chloride homopolymers and copolymers such as vinyl chloride/vinyl acetate; vinyl chloride/ethylene; vinyl chloride/vinylidene chloride and like polymeric materials are preferred. Natural and synthetic resins and gums can also be used, the only requirement being that they be soluble in the reaction system.

Because water reacts with isocyanate to form ureas and biurets, it is preferred to dry the granular substrate material under vacuum prior to use. This is particularly true of organic substrates such as corn cob grits which may have a relatively high moisture content. On the other hand, with certain relatively dry substrates, such as coal, such pretreatment may not be necessary. Since it is usually desirable for economic reasons to make certain that complete conversion of the active hydrogen compound occurs it is usually preferable to use an excess of the isocyanate reactant. Suitable ranges normally fall within a ratio of 1.1:1.0 to 2:1 isocyanate to active compound on an equivalent basis.

The amount of granular material used can range from very large amounts where very high dilution is required to relatively small amounts where a more concentrated product is required. Where high dilution is desired it may be necessary to use solvent to obtain uniform wetting and distribution of the active ingredient over the substrate. It is sometimes difficult to obtain a concentration of greater than about 50% by weight of active ingredient in a single pass. If higher concentrations are desired the granular product of the first reaction can be used a second time to thereby increase the concentration of the active ingredient. In most cases the weight ratio of granular material to the combined weight of the isocyanate and the active hydrogen reactants will be from about 1:1 to about 100:1 to yield products varying in concentration of active ingredient from about 1% to about 50% by weight with the preferred concentrations being from about 5% to about 25% by weight.

In conducting the process of this invention the sequence of addition of the reactants has little or no significance. One reactant (with solvent, if required) may be added to the granular substrate in a stirred vessel and then the other added or both reactants may be added simultaneously. Additives such as catalysts and dust binding agents are preferably dissolved in one of the reactants prior to addition.

Reaction temperatures may vary from 0° to 100° C. or higher. Lower temperatures are undesirable due to slower reaction rates. The upper temperature limit is normally dictated by the thermal stability of the product. Reaction times vary from about 1 to about 5 hours to ensure completion. Upon completion, unreacted materials and any solvent or catalyst present are removed by evaporation under reduced pressure. The product is then screened and de-dusted, if necessary, prior to packaging for use. Should the product consist of very fine particles, they may be compressed into plugs and ground into the desired particle size prior to de-dusting and screening.

The following examples are provided to more clearly illustrate our invention.

EXAMPLE 1

Corn cob grits (200 g) that had been vacuum dried at 110° C. were placed in 1 liter reaction glask provided with stirrer, additional gunnel and dry-ice condenser. To the stirred corn cobs was added from the additional funnel at room temperature a solution of 2.3 g VYHD resin (VYHD resin is a commercial vinyl resin prepared by copolymerizing 86 percent by weight vinyl chloride and 14 percent by weight vinyl acetate) in 13.6 g MIC (methyl isocyanate) (0.238 mole; 100% excess) within 30 minutes. The additional funnel was then charged with a solution of 0.26 g trimethylamine (0.004 mole) in 16.1 g (90%) 2-methyl-2-methylthiopropionaldehyde oxime (Aldicarb Oxime) (0.119 mole) (prepared by the method) described in U.S. 3,217,037 and this solution was added within a half-four period. The reaction flask was then placed in a water bath of 50° C. for 2 hours while constantly stirring the reaction mixture. Vacuum drying of the product at $\leq$ 1 mm Hg. at 50° for 30 minutes afforded a product with an Aldicarb content of 9.5 percent. (Theory: 10.1 percent)

Microscopic inspection of the formulated product revealed an excellent physical appearance which was judged to be superior to equivalent material made by the impregnation technique.

EXAMPLE 2

Example 1 was repeated except that the sequence of addition was reversed: The trimethylamine in Aldicarb Oxime solution was added first, followed by the addition of VYHD resin in MIC solution. Assays of the finished product, which again exhibited excellent physical appearance, indicated an Aldicarb content of 9.8 percent (Theory: 10.1 percent).

EXAMPLE 3

Example 2 was repeated except that the MIC was reduced from 13.6 g (100 percent excess; 0.238 mole) to 10.2 g (50 percent excess; 0.179 mole). The product obtained was similar to that of Example 1 and 2 and assayed 9.5 percent Aldicarb (Theory: 10.1 percent).

EXAMPLE 4

Example 2 was repeated except that the amount of MIC was further reduced to 8.2 g (20 percent excess; 0.144 mole). The product obtained was comparable to formulated material made by the impregnation technique and analyzed for 9.7 percent Aldicarb (Theory: 10.1 percent).

EXAMPLE 5

Corn cobs (200 g.) were treated as described in Example 2 with a solution of 0.3 g trimethylamine in 24.6 g. Aldicarb Oxime (98%, 0.1815 mole) and a solution of 3.45 g. VYHD resin in 20.7 g MIC (0.363 mole). The resulting product had an Aldicarb content of 14.7 percent (Theory: 14.9 percent).

EXAMPLE 6

Corn cobs (200 g.) were treated as described in Example 2 with a solution of 0.3 g. trimethylamine in 32.8 g. Aldicarb Oxime (98%, 0.242 mole) and a solution of 4.6 g. resin VYHD in 27.6 g. MIC (0.484 mole). The resulting product contained 18.8 percent Aldicarb (Theory: 18.7 percent).

EXAMPLE 7

Fluidized coke (196 g. 30–50 mesh) was treated as described in Example 2 with a solution of 0.3 g. trimethylamine in 16.1 g. Aldicarb Oxime (98 percent, 0.119 mole) and a solution of 2.3 g. Resin VYHD in 13.6 g. MIC (0.238 mole). The resulting product which analyzed for 10.1 percent Aldicarb (Theory: 10.3 percent), had an asbestos-like appearance due to dimethylurea crystal accumulation (formed from the MIC and the moisture in the substrate).

EXAMPLE 8

Coal (200 g. 16/35 mesh) which had been vacuum dried at 110° C., was treated as described in Example 2. The smoothly coated product had an Aldicarb content of 8.9 percent (Theory: 10.1 percent).

EXAMPLE 9

Vacuum dried coal (200 g. 16/35 mesh) was treated as described in Example 5. The resulting product analyzed for 14.4 percent Aldicarb (Theory: 14.9 percent).

EXAMPLE 10

Vacuum dried coal (165 g. 16/35 mesh) was treated first with a solution of 0.25 g. trimethylamine in 27.1 g. Aldicarb Oxime (98%, 0.20 mole) and then with a solution of 3.8 g. Resin VYHD in 22.8 g. MIC (0.40 mole). The resulting formuation had an Aldicarb assay of 18.5 percent (Theory: 18.7 percent).

EXAMPLE 11

Petroleum coke (180 g., Fostoria Cold Mold Mix No. 7) together with 14.5 g. Aldicarb Oxime (96% purity, 0.104 mole) and 9.0 g. MIC (0.157 mole) was placed in a one liter jacketed stainless steel reactor equipped with a temperature recorder and a double scraped-wall stirrer. The mixture was stirred for 3 hours with the reactor jacket temperature being kept at 10°–15° C. during the first 1.5 hours by circulating cold water through the jacket. The jacket temperature was then allowed to rise slowly to 20°–25° C. during the remaining 1.5 hours. At the end of this period, excess MIC was removed from the system under reduced pressure. After air drying over night, the mixture was obtained as a hard, granular, prill-like product. The products from individual foru runs were combined and screened to give the following.

| Mesh Size | Grams | Per cent of Total | Aldicarb Content % |
|---|---|---|---|
| >10 | 56 | 7.2 | — |
| 10/16 | 264 | 33.8 | 9.5 |
| 16/35 | 376 | 48.3 | 9.9 |
| <35 | 84 | 10.7 | — |

EXAMPLE 12

Example 11 was repeated and the prill-like, granular product obtained was ground to pass 40 mesh and compressed under 25–30 tons of force into plugs. The plugs were then granulated and screened into 10/16 (Aldicarb content 10.6 percent) and 16/35 mesh granulars (Aldicarb content 10.25 percent).

EXAMPLE 13

Example 12 was repeated except that Aldicarb Oxime of 85 percent purity was used instead of the higher (96 percent) purity Aldicarb Oxime used in Example 12. Assays of the 10/16 and 16/35 mesh material ran 11.6 and 9.6 percent Aldicarb, respectively.

EXAMPLE 14

A jacketed stainless steel reactor at 12° C. was charged with 180 g. of petroleum coke (cold mold mix #18), 14.5 g. 85 percent purity Aldicarb Oxime, and 9.5 g. MIC (50 percent excess). After mixing for 1.5 hours an additional 18.1 g. Aldicarb Oxime and 11.8 g. MIC (50 percent excess) was added and stirring was continued for 1.5 hours. At the end of this period a final charge of 10.9 g. Aldicarb Oxime and 7.1 g. MIC (50 percent excess) was made and the mixture was stirred for 3 hours. The products from two runs were combined and screened to give the following results:

| Mesh Size | Grams | Per cent of Total | Aldicarb Content (%) |
|---|---|---|---|
| 10/16 | 226 | 47.6 | 21.7 |
| 16/35 | 152 | 32.0 | 21.7 |
| Heavies | 42 | 8.8 | — |
| Fines | 55 | 11.6 | — |
| | 475 | 100.0 | |

EXAMPLE 15

In a pilot-plant size jacketed stainless steel mixer, 15 pound of corn cob grits were dried during an 8-to-12-hour period with stirring under reduced pressure (200–300 mm Hg) and a jacket temperature of 50° C. After cooling to 25°–35° C., 583 g. of Aldicarb Oxime (94%, 4.12 mole) containing 19.5 g. of trimethyl amine was poured over the substrate. The lid was secured and the mixture stirred for 30 minutes. MIC (354 g., 6.21 mole) containing 78 g of dissolved resin VYHD was then added over a 15-to 30-minute period. The reaction mixture was heated to 50° C. and, while stirring, was kept at this temperature for 2–3 hours. Vacuum was then applied very slowly over a period of one hour and after holding at full vacuum for an additional hour, the product was cooled and discharged. The discharged formulation was screened to give the following products:

| Screened Product | Weight | Per cent of Total | Aldicarb Content (%) |
|---|---|---|---|
| +14 | 10 g | 0.13 | — |
| −14/+40 | 16.3 lbs | 98.87 | 9.9 |
| −40 | 34 g | 0.45 | — |
| scrap | 44 g | 0.55 | — |

EXAMPLE 16

Example 15 was repeated except that solutions of 10.0 g trimethylamine in 874 g of Aldicarb Oxime (94%, 6.18 mole) and 118 g of resin VYHD in 531 g of MIC were employed. The discharged product had the following composition:

| Screened Product | Weight | Per cent of Total | Aldicarb Content (%) |
|---|---|---|---|
| +14 | 9 g | 0.12 | — |
| −14/+14 | 17 lbs | 98.53 | 13.5 |
| −40 | 36 g | 0.46 | — |
| scrap | 70 g | 0.89 | — |

EXAMPLES 17 to 31

A series of fifteen separate chemically distinct compositions were prepared by the process of this invention to demonstrate the universal applicability of this process to all reactions between an isocyanate compound and an active hydrogen carrying compound. The reactions were carried out batchwise in simple laboratory equipment using 200 g of dried corncob grits. The general procedure consisted of adding the hydroxyl or amine type precursor containing dissolved trimethylamine (TMA) catalyst to the stirred substrate at room temperature, followed by the addition of a solution of VYHD resin (dust binding agent) in the isocyanate. An average reaction time of two hours at 50° C. was sufficient to complete the reaction. The products were then freed of catalyst and excess reactants by evaporation under reduced pressure.

Although TMA was employed as a catalyst in each of these experiments these reactions will proceed without catalysis, but at a slower rate. To achieve complete conversion of the less volatile reactant, an excess of the more volatile reactant was used (e.g., MIC, isopropanol or dimethylamine, respectively). In the cases where one of the reactants was a solid (or a gas, such as dimethylamine) a minimal amount of a low boiling solvent, such as acetone ($Me_2CO$), chloroform ($CHCl_3$), or acetonitrile (MeCN) was employed. Produt yields and identities were determined by extraction and infrared spectroscopy of the extracted material. Whenever spectral data of the active ingredient were not available, the carbamoylation reaction was first run in the absence of the substrate and an IR scan of the purified product was obtained. The types of reactants used include phenols, alcohols, oximes and amines as well as MIC, phenyl isocyanate and m-chlorophenyl isocyanate.

The following is illustrative of the procedure followed in these experiments:

A 1-liter reaction flask provided with mechanical stirrer, thermometer, dry ice condenser, and addition funnel was charged with 200 g of dired corncob grits. To the stirred substrate, 15.5 g m-cresol (95%) containing 0.5 g TMA was added dropwise within 15 minutes at room temperature. Next, a solution of 1.6 g VYHD resin in 11.6 g MIC was added under the same conditions. By means of a water bath, the mixture was heated to 50° C. for two hours. The moist product was transferred to a 1-liter single neck flask and connected to a rotary evaporator. While heating in a water bath (50° C.), vacuum (0.5 mm) was applied for 45 minutes to remove TMA and excess MIC. A sample of the dry formulation (11.766 g) was extracted (0.5 hr) with acetone in a Saxhlet extractor. After evaporation of the acetone in vacuo a solid residue weighing 1.42 g remained. Allowing for 0.10 g VYHD resin, the active material amounted to 1.32 g = 11.2 percent. The IR spectrum of the extract was identical to the one obtained from the pure compound, 3-methyl phenyl-N-methylcarbamate. (Tsumacide)

The details of each of the fifteen experiments and the results obtained are set forth in Table I below. Dried corn cob grits were used in each of these experiments as the substrate material.

TABLE I

| Example No. | Reactants 1 | Reactants 11 | Temp. (° C) | Time (hrs) | Product | MP (° C) | Solvent | % Active |
|---|---|---|---|---|---|---|---|---|
| 17 | m-Cresol | MIC | 58 | 1.5 | 3-Methylphenyl-N-methylcarbamate | 75-6 | None | 11.2 |
| 18 | 3,4-Dimethylphenol | MIC | 60 | 2.0 | 3,4-Dimethylphenyl-N-methylcarbamate | 79-80 | $Me_2CO$ | 10.8 |
| 19 | 3,4,5-Trimethylphenol | MIC | 58 | 3.0 | 3,4,5-Trimethylphenyl-N-methylcarbamate | 118-19 | $Me_2CO$ | 11.1 |
| 20 | -Naphthol | MIC | — | — | 1-Naphthyl-N-methyl carbamate | 142 | $CHCl_3$ | 10.2 |
| 21 | o-Chlorophenol | MIC | 60 | 0.7 | 2-Chlorophenyl-N-methylcarbamate | 89-90 | None | 9.6 |
| 22 | Isopropanol | PhNCO | 50 | 0.7 | Isopropyl-N-phenylcarbamate | 85-6 | None | 9.9 |

TABLE I-continued

| Example No. | Reactants 1 | Reactants 11 | Temp. (°C) | Time (hrs) | Product | MP (°C) | Solvent | % Active |
|---|---|---|---|---|---|---|---|---|
| 23 | 3,4-Dichlorobenzyl alcohol | MIC | 58 | 1.5 | 3,4-Dichloro-benzyl-N-methyl-carbamate | 53-4 | CHCl$_3$ | 9.9 |
| 24 | m-Isopropylphenol | MIC | 58 | 1.0 | 3-Isopropyl-phenyl-N-methyl-carbamate | 72-3 | None | 9.7 |
| 25 | Dimethylamine | PhNCO | 57 | 1.0 | 3-Phenyl-1,1-dimethyl urea | 133-4 | CHCl$_3$ | 9.3 |
| 26 | 2-Oximino-1,4-dithiane | MIC | 58 | 2.0 | 2-(N-methyl-carbamoyl)-oximino-1,4-dithiane | 87-9 | MeCN | 8.8 |
| 27 | 1-Methylthio-acetaldoxime | MIC | — | — | 1-Methylthio-acetaldehyde O-(methyl-carbamoyl) oxime | 78-9 | Me$_2$CO | 5.5 |
| 28 | 1-(Methylthio)-methyl-2,2-dimethyl propion-aldoxime | MIC | — | — | 1-(Methylthio)-methyl-2,2-dimethyl propion-aldehyde O-(methyl-carbomoyl) oxime | 53.5 | None | 5.5 |
| 29 | Isopropanol | m-Chloro-phenyliso-cyanate | — | — | Isopropyl-N-3-chloro-phenyl-carbamate | 38-9 | None | 4.3 |
| 30 | m-Amylphenols | MIC | — | — | 3-Amylphenyl-N-methyl carbamate | 26-39 | None | 6.3 |
| 31 | 2,6-Di-t-butyl-p-cresol | MIC | — | — | 2,6-Di-t-butyl-tolyl N-methyl-carbamate | 200-01 | Me$_2$CO | 5.0 |

In addition to the compositions whose preparation is described above it will be appreciated that a multitude of other compositions can be prepared in like manner using the process of this invention. By way of further illustration the following biologically active compositions can be prepared by this method simply by reacting the appropriate isocyanate precursor with the appropriate active hydrogen containing precursor:

4-Benzothienyl-N-methylcarbamate
N-(3,3-Dimethylureido) phenyl t-butyl-carbamate
Dimethyl phosphate of 3-hydroxy-N-methyl-cis-crotonamide
Methyl 1-(butylcarbamoyl)-2-benzimidazole carbamate
Methyl m-hydroxycarbanilate m-methylcarbanilate
m-(1-Methylbutyl)phenylmethyl carbamate
m-(1-Ethylpropyl)phenylmethylcarbamate
2,3-Dihydro-2,2-dimethyl-7-benzofuranyl methyl carbamate
O-(Methyl-2-propinylamino)phenyl N-methylcarbamate
Isopropyl m-chlorocarbanilate
0,0-Dimethyl S-(N-methylcarbamoylmethyl) phosphonodithioate
4-Dimethylamino-m-tolylmethylcarbamate
4-Chloro-2-butynyl N-(3-chlorophenyl)carbamate
4-Benzothioenyl-N-methylcarbamate
Dimethylamino xylyl methcarbamate
3-(3,4-Dichlorophenyl)-1,1-dimethylurea
3-[(1-Ethylpropyl)phenyl methylcarbamate] 4-(Methylthio)-3,5-xylyl methylcarbamate]
3-(3,4-dichlorophenyl)-1-methoxy-1-methylurea
N-(4-chlorophenyl)-N$^1$-methoxy-N$^1$-methyl-urea
Methyl dichlorophenylcarbamate
(3-(p-Chlorophenyl)-1,1-dimethylurea
1-n-Butyl-3-(3,4-dichlorophenyl)-1-mwethylurea
2-Isopropoxyphenyl N-methylcarbamate
(1-(2-Methylcyclohexyl)-3-phenyl urea
endo-3-chloro-exo-6-cyano-2-norbornanone o-(methylcarbamoyl)oxime
3,4:Xylenol, 6-chloro-methylcarbamate
3-(α-Acetonylbenzyl)-4-hydroycoumarin

We claim:

1. In a process for the production of carbamate or urea compositions by the reaction of an organic isocyanate compound and an organic active hydrogen containing compound, the improvement which comprises conducting such reaction in the presence of inert solid granular material.

2. Process according to claim 1 wherein said solid material is essentially anhydrous having a water content of less than about one percent (1%) by weight.

3. Process according to claim 1 wherein an excess amount of organic isocyanate in relation to the amount of active hydrogen containing compound is employed.

4. Process according to claim 1 wherein said reaction is conducted in the presence of a synthetic or natural resin or gum as a dust binding agent.

5. Process according to claim 1 wherein said reaction is conducted essentially in the absence of any liquid solvent.

6. Process according to claim 1 wherein a stoichiometric excess amount of the more volatile of the two reactive starting materials is provided.

7. Process according to claim 1 wherein said active hydrogen containing compound is an alcohol, hydroxyaromatic compound, ammonia or a primary or secondary amine compound.

8. Process according to claim 1 wherein said inert granular material is clay, peat, mica, vermiculite, coal, corncob, tobacco skin, coconut shell, walnut shell, wood or bark.

9. Process according to claim 8 wherein said granular material has a particle size of from about 10 to about 60 mesh.

10. Process according to claim 1 wherein said isocyanate compound is methyl isocyanate and said active hydrogen containing compound is 2-methyl-2-methylthiopropionaldehyde oxime.

11. Process according to claim 1 wherein said isocyanate compound is methyl isocyanate and said active hydrogen containing compound is 1-methylthioacetaldoxime.

12. Process according to claim 1 wherein said isocyanate compound is methyl isocyanate and said active hydrogen containing compound is m-cresol.

13. Process according to claim 1 wherein said isocyanate compound is methyl isocyanate and said active hydrogen containing compound is 3,4-dimethylphenol.

14. Process according to claim 1 wherein said isocyanate compound is methyl isocyanate and said active hydrogen containing compound is 1-(methylthio)methyl-2,2-dimethyl propionaldoxime.

15. Process according to claim 1 wherein said isocyanate compound is methyl isocyanate and said active hydrogen containing compound is 2,6-di-t-butyl-p-cresol.

16. Process according to claim 1 wherein said isocyanate compound is phenylisocyanate and said active hydrogen containing compound is isopropanol.

17. Process according to claim 1 wherein said isocyanate compound is phenylisocyanate and said active hydrogen containing compound is dimthylamine.

18. Process according to claim 1 wherein said isocyanate compound is m-chlorophenylisocyanate and said active hydrogen containing compound is isopropanol.

19. A method of producing Aldicarb which comprises reacting methyl isocyanate and 2-methyl-2-(methylthio)propionaldehyde oxime in the presence of an inert solid granular material.

20. The method of claim 19 in which said solid material is essentially anhydrous having a water content of less than about one percent (1%) by weight.

21. The method of claim 19 in which a stoichiometric excess of methyl isocyanate is used.

22. The method of claim 19 in which said reaction is conducted in the presence of a synthetic or natural resin or gum.

23. A method of producing Aldicarb dispersed on a granular solid substrate which comprises reacting methyl isocyanate and 2-methyl-2-(methylthio)propionaldehyde oxime in the presence of an essentially anhydrous inert solid granular material; a catalytic quantity of trimethylamine and up to about thirty percent by weight of the reactive ingredients of a synthetic resinous dust binding agent and thereafter drying the resulting product under vacuum.

24. In a process for the production of biologically active carbamate or urea compositions by the reaction of an organic isocyanate compound and an organic active hydrogen containing compound, the improvement which comprises conducting such reaction in the presence of a quantity of inert solid granular material at least about equivalent by weight to the combined total weight of organic isocyanate compound and organic active hydrogen containing compound.

25. Process according to claim 24 wherein said solid material is essentially anhydrous having a water content of less than about one percent (1%) by weight.

26. Process according to claim 24 wherein said reaction is conducted in the presence of a synthetic or natural resin or gum as a dust binding agent is employed.

27. Process according to claim 24 wherein said reaction is conducted essentially in the absence of any liquid solvent.

28. Process according to claim 24 wherein a stoichiometric excess amount of the more volatile of the two reactive starting materials is provided.

* * * * *

UNITED STATES PATENT AND TRADEMARK OFFICE
CERTIFICATE OF CORRECTION

PATENT NO. : 4,138,422
DATED : February 6, 1979
INVENTOR(S) : John K-F. Chan et al It is certified that error appears in the above-identified patent and that said Letters Patent are hereby corrected as shown below:

Column 8, line 17, "Produt" should read --Product--.
Column 9, line 63, "mwetylurea" should read --methylurea--.

Signed and Sealed this

Eighth Day of May 1979

[SEAL]

Attest:

RUTH C. MASON
Attesting Officer

DONALD W. BANNER
Commissioner of Patents and Trademarks